(12) United States Patent
Dittman et al.

(10) Patent No.: US 7,968,038 B2
(45) Date of Patent: Jun. 28, 2011

(54) LARGE DIAMETER DELIVERY CATHETER/SHEATH

(75) Inventors: Jay A. Dittman, Bloomington, IN (US); David A. Drewes, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/719,228

(22) Filed: Mar. 8, 2010

(65) Prior Publication Data

US 2010/0163159 A1    Jul. 1, 2010

Related U.S. Application Data

(62) Division of application No. 10/823,176, filed on Apr. 13, 2004, now Pat. No. 7,704,245.

(60) Provisional application No. 60/462,632, filed on Apr. 14, 2003.

(51) Int. Cl.
*B29C 65/18* (2006.01)
*A61M 25/00* (2006.01)

(52) U.S. Cl. .............. 264/342 R; 264/263; 264/271.1; 156/143; 604/523

(58) Field of Classification Search .............. 264/342 R
See application file for complete search history.

(56) References Cited

U.S. PATENT DOCUMENTS

| | | | |
|---|---|---|---|
| 2,437,542 A | 3/1948 | Krippendorf | 128/349 |
| 2,857,915 A | 10/1958 | Sheridan | 128/349 |
| 3,174,851 A | 3/1965 | Buehler et al. | 75/170 |
| 3,228,894 A | 1/1966 | Jeckel | 252/478 |
| 3,351,463 A | 11/1967 | Rozner et al. | 75/170 |
| 3,370,587 A | 2/1968 | Vizcarra | 128/214.4 |
| 3,416,531 A | 12/1968 | Edwards | 128/348 |
| 3,485,234 A | 12/1969 | Stevens | 128/2 |
| 3,568,660 A | 3/1971 | Crites et al. | 128/2 |
| 3,608,555 A | 9/1971 | Greyson | 128/348 |
| 3,612,038 A | 10/1971 | Halligan | 128/2.05 R |
| 3,618,614 A | 11/1971 | Flynn | 128/348 |
| 3,746,003 A | 7/1973 | Blake et al. | 128/349 B |
| 3,749,134 A | 7/1973 | Slingluff et al. | 138/177 |
| 3,753,700 A | 8/1973 | Harrison et al. | 75/175.5 |
| 3,866,599 A | 2/1975 | Johnson | 128/2 L |
| 3,890,976 A | 6/1975 | Bazell et al. | 128/351 |
| 3,890,977 A | 6/1975 | Wilson | 128/418 |
| 3,924,632 A | 12/1975 | Cook | 128/348 |
| 3,935,857 A | 2/1976 | Co | 128/2.05 |
| 3,995,623 A | 12/1976 | Blake et al. | 128/2.06 |

(Continued)

FOREIGN PATENT DOCUMENTS

WO    WO 01/07231 A1    2/2001

*Primary Examiner* — Yogendra N Gupta
*Assistant Examiner* — Alison Hindenlang
(74) *Attorney, Agent, or Firm* — Brinks Hofer Gilson & Lione

(57) ABSTRACT

A large diameter, flexible, kink-resistant, delivery catheter or sheath for percutaneous delivery of a contained and implantable medical device in the vasculature of a patient. The delivery catheter or sheath includes a reinforcement such as a flat wire coil with uniform spacing between the turns, which is compression fitted about an inner, lubricous PTFE tube. The delivery catheter or sheath further includes an outer tube of a heat formable polyamide material which is heat formed and compressed through the spaces between the turns of the wire coil to mechanically connect to a roughened outer surface of the inner tube. A polymeric radiopaque marker tube may be positioned at the distal end of the coil and between the inner and outer tubes for radiographic visualization. A side port may also be positioned thereat for the infusion of contrast media.

12 Claims, 3 Drawing Sheets

U.S. PATENT DOCUMENTS

| | | | |
|---|---|---|---|
| 4,015,601 A | 4/1977 | Bokros et al. | 128/214 R |
| 4,024,873 A | 5/1977 | Antoshkiw et al. | 128/349 B |
| 4,029,104 A | 6/1977 | Kerber | 128/348 |
| 4,099,425 A | 7/1978 | Moore | 74/501 P |
| 4,117,836 A | 10/1978 | Erikson | 128/2.05 R |
| 4,169,464 A | 10/1979 | Obrez | 128/657 |
| 4,184,497 A | 1/1980 | Kolff et al. | 131/213 A |
| 4,196,731 A | 4/1980 | Laurin et al. | 128/214 R |
| 4,248,234 A | 2/1981 | Assenza et al. | 128/348 |
| 4,265,276 A | 5/1981 | Hatada et al. | 138/177 |
| 4,276,874 A | 7/1981 | Wolvek et al. | 128/1 D |
| 4,279,252 A | 7/1981 | Martin | 128/349 R |
| 4,306,566 A | 12/1981 | Sinko | 128/658 |
| 4,329,993 A | 5/1982 | Lieber et al. | 128/349 |
| 4,345,602 A | 8/1982 | Yoshimura et al. | 128/349 R |
| 4,361,152 A | 11/1982 | Patel | 604/99 |
| 4,362,163 A | 12/1982 | Krick | 604/280 |
| 4,368,730 A | 1/1983 | Sharrock | 604/158 |
| 4,385,635 A | 5/1983 | Ruiz | 128/658 |
| 4,425,919 A | 1/1984 | Alston, Jr. et al. | 128/658 |
| 4,464,176 A | 8/1984 | Wijayarathna | 604/164 |
| 4,484,586 A | 11/1984 | McMickle et al. | 128/786 |
| 4,498,473 A | 2/1985 | Gereg | 128/207.15 |
| 4,504,268 A | 3/1985 | Herlitze | 604/170 |
| 4,516,972 A | 5/1985 | Samson | 604/282 |
| 4,531,943 A | 7/1985 | Van Tassel et al. | 604/280 |
| 4,547,193 A | 10/1985 | Rydell | 604/282 |
| 4,551,292 A | 11/1985 | Fletcher et al. | 264/139 |
| 4,563,181 A | 1/1986 | Wijayarathna et al. | 604/280 |
| 4,571,240 A | 2/1986 | Samson et al. | 604/96 |
| 4,577,543 A | 3/1986 | Wilson | 87/11 |
| 4,596,563 A | 6/1986 | Pande | 604/264 |
| 4,610,674 A | 9/1986 | Suzuki et al. | 604/282 |
| 4,627,844 A | 12/1986 | Schmitt | 604/264 |
| 4,636,346 A | 1/1987 | Gold et al. | 264/139 |
| 4,639,246 A | 1/1987 | Dudley | 604/159 |
| 4,694,838 A | 9/1987 | Wijayarthna et al. | 128/658 |
| 4,696,304 A | 9/1987 | Chin | 128/673 |
| 4,705,511 A | 11/1987 | Kocak | 604/282 |
| 4,721,115 A | 1/1988 | Owens | 128/713 |
| 4,737,153 A | 4/1988 | Shimamura et al. | 604/282 |
| 4,739,768 A | 4/1988 | Engelson | 128/658 |
| 4,747,840 A | 5/1988 | Ladika et al. | 604/281 |
| 4,758,221 A | 7/1988 | Jureidini | 604/95 |
| 4,762,130 A | 8/1988 | Fogarty | 128/348 |
| 4,775,371 A | 10/1988 | Mueller, Jr. | 604/280 |
| 4,806,182 A | 2/1989 | Rydell et al. | 156/211 |
| 4,817,613 A | 4/1989 | Jaraczewski et al. | 128/658 |
| 4,832,681 A | 5/1989 | Lenck | 600/34 |
| 4,840,622 A | 6/1989 | Hardy | 604/264 |
| 4,842,590 A | 6/1989 | Tanabe et al. | 604/282 |
| 4,863,442 A | 9/1989 | DeMello et al. | 604/282 |
| 4,883,058 A | 11/1989 | Ruiz | 128/654 |
| 4,884,579 A | 12/1989 | Engelson | 128/772 |
| 4,886,506 A | 12/1989 | Lovgren et al. | 604/280 |
| 4,898,591 A | 2/1990 | Jang et al. | 604/282 |
| 4,899,787 A | 2/1990 | Ouchi et al. | 138/131 |
| 4,960,410 A | 10/1990 | Pinchuk | 604/96 |
| 4,963,306 A | 10/1990 | Weldon | 264/101 |
| 4,985,022 A | 1/1991 | Fearnot et al. | 604/282 |
| 4,994,069 A | 2/1991 | Ritchart et al. | 606/191 |
| 5,019,057 A | 5/1991 | Truckai | 604/282 |
| 5,037,404 A | 8/1991 | Gold et al. | 604/282 |
| 5,057,092 A | 10/1991 | Webster, Jr. | 604/282 |
| 5,069,673 A | 12/1991 | Shwab | 604/280 |
| 5,069,674 A | 12/1991 | Fearnot et al. | 604/282 |
| 5,078,702 A | 1/1992 | Pomeranz | 604/280 |
| 5,085,649 A | 2/1992 | Flynn | 604/282 |
| 5,088,991 A | 2/1992 | Weldon | 604/280 |
| 5,116,652 A | 5/1992 | Alzner | 428/36.9 |
| 5,156,785 A | 10/1992 | Zdrahala | 264/108 |
| 5,160,559 A | 11/1992 | Scovil et al. | 156/73.6 |
| 5,163,431 A | 11/1992 | Griep | 128/658 |
| 5,171,232 A | 12/1992 | Castillo et al. | 604/280 |
| 5,176,660 A | 1/1993 | Truckai | 604/282 |
| 5,178,158 A | 1/1993 | De Toledo | 128/772 |
| 5,180,376 A | 1/1993 | Fischell | 604/282 |
| 5,217,482 A | 6/1993 | Keith | 606/194 |
| 5,221,255 A | 6/1993 | Mahurkar et al. | 604/43 |
| 5,221,270 A | 6/1993 | Parker | 604/282 |
| 5,226,911 A | 7/1993 | Chee et al. | 606/191 |
| 5,234,416 A | 8/1993 | Macaulay et al. | 604/282 |
| 5,248,305 A | 9/1993 | Zdrahala | 604/280 |
| 5,250,071 A | 10/1993 | Palermo | 606/198 |
| 5,254,107 A | 10/1993 | Soltesz | 604/282 |
| 5,261,916 A | 11/1993 | Engelson | 606/108 |
| 5,279,596 A | 1/1994 | Castaneda et al. | 604/282 |
| 5,286,259 A | 2/1994 | Ganguly et al. | 604/96 |
| 5,290,230 A | 3/1994 | Ainsworth et al. | 604/96 |
| 5,294,325 A | 3/1994 | Liu | 204/418 |
| 5,304,194 A | 4/1994 | Chee et al. | 606/191 |
| 5,304,195 A | 4/1994 | Twyford, Jr. et al. | 606/191 |
| 5,306,252 A | 4/1994 | Yutori et al. | 604/164 |
| 5,306,262 A | 4/1994 | Weldon | 604/281 |
| 5,308,342 A | 5/1994 | Sepetka et al. | 604/282 |
| 5,312,415 A | 5/1994 | Palermo | 606/108 |
| 5,314,418 A | 5/1994 | Takano et al. | 604/282 |
| 5,334,169 A | 8/1994 | Brown et al. | 604/282 |
| 5,334,171 A | 8/1994 | Kaldany | 604/282 |
| 5,336,205 A | 8/1994 | Zenzen et al. | 604/280 |
| 5,342,295 A | 8/1994 | Imran | 604/43 |
| 5,342,383 A | 8/1994 | Thomas | 606/190 |
| 5,342,386 A | 8/1994 | Trotta | 606/194 |
| 5,348,536 A | 9/1994 | Young et al. | 604/43 |
| 5,356,388 A | 10/1994 | Sepetka et al. | 604/164 |
| 5,380,304 A | 1/1995 | Parker | 604/282 |
| 5,397,306 A | 3/1995 | Nobuyoshi et al. | 604/96 |
| 5,403,292 A | 4/1995 | Ju | 604/282 |
| 5,423,773 A | 6/1995 | Jimenez | 604/282 |
| 5,472,435 A | 12/1995 | Sutton | 604/282 |
| 5,484,565 A | 1/1996 | Larsen et al. | 264/230 |
| 5,489,269 A | 2/1996 | Aldrich et al. | 604/95 |
| 5,496,294 A | 3/1996 | Hergenrother et al. | 604/282 |
| 5,514,236 A | 5/1996 | Avellanet et al. | 156/154 |
| 5,531,721 A | 7/1996 | Pepin et al. | 604/282 |
| 5,545,149 A | 8/1996 | Brin et al. | 604/265 |
| 5,569,218 A | 10/1996 | Berg | 604/282 |
| 5,599,325 A | 2/1997 | Ju et al. | 604/282 |
| 5,599,326 A | 2/1997 | Carter | 604/282 |
| 5,601,538 A | 2/1997 | Deem | 604/280 |
| 5,603,705 A | 2/1997 | Berg | 604/282 |
| 5,658,263 A | 8/1997 | Dang et al. | 604/280 |
| 5,674,208 A | 10/1997 | Berg et al. | 604/282 |
| 5,676,659 A | 10/1997 | McGurk | 604/282 |
| 5,700,253 A | 12/1997 | Parker | 604/282 |
| 5,702,373 A | 12/1997 | Samson | 604/282 |
| 5,725,513 A | 3/1998 | Ju et al. | 604/280 |
| 5,755,704 A | 5/1998 | Lunn | 604/282 |
| 5,769,830 A | 6/1998 | Parker | 604/282 |
| 5,772,641 A | 6/1998 | Wilson | 604/280 |
| 5,791,036 A | 8/1998 | Goodin et al. | 29/423 |
| 5,792,124 A | 8/1998 | Horrigan et al. | 604/282 |
| 5,807,350 A | 9/1998 | Diaz | 604/256 |
| 5,811,043 A | 9/1998 | Horrigan et al. | 264/138 |
| 5,836,925 A | 11/1998 | Soltesz | 604/280 |
| 5,843,031 A | 12/1998 | Hermann et al. | 604/95 |
| 5,851,203 A | 12/1998 | Van Muiden | 604/282 |
| 5,860,963 A | 1/1999 | Azam et al. | 604/280 |
| 5,897,537 A | 4/1999 | Berg et al. | 604/282 |
| 5,906,605 A | 5/1999 | Coxum | 605/525 |
| 5,911,715 A | 6/1999 | Berg et al. | 604/525 |
| 5,938,653 A | 8/1999 | Pepin | 604/527 |
| 5,947,939 A | 9/1999 | Mortier et al. | 604/280 |
| 5,951,495 A | 9/1999 | Berg et al. | 600/585 |
| 5,951,929 A | 9/1999 | Wilson | 264/139 |
| 5,954,651 A | 9/1999 | Berg et al. | 600/434 |
| 5,964,971 A | 10/1999 | Lunn | 156/86 |
| 5,971,975 A | 10/1999 | Mills et al. | 604/527 |
| 5,972,441 A | 10/1999 | Campbell et al. | 428/34.1 |
| 5,976,120 A | 11/1999 | Chow et al. | 604/525 |
| 5,980,505 A | 11/1999 | Wilson | 604/525 |
| 6,025,044 A | 2/2000 | Campbell et al. | 428/36.91 |
| 6,027,779 A | 2/2000 | Campbell et al. | 428/36.91 |
| 6,045,547 A | 4/2000 | Ren et al. | 604/525 |
| 6,059,769 A | 5/2000 | Lunn et al. | 604/523 |
| 6,077,258 A | 6/2000 | Lange et al. | 604/527 |
| 6,090,099 A | 7/2000 | Samson et al. | 604/527 |

| Patent | Date | Inventor | Class |
|---|---|---|---|
| 6,103,037 A | 8/2000 | Wilson | 156/158 |
| 6,106,540 A | 8/2000 | White et al. | 606/191 |
| 6,152,912 A | 11/2000 | Jansen et al. | 604/526 |
| 6,159,198 A | 12/2000 | Gardeski et al. | 604/523 |
| 6,165,165 A | 12/2000 | Cecchi et al. | 604/523 |
| 6,168,588 B1 | 1/2001 | Wilson | 604/525 |
| 6,171,296 B1 | 1/2001 | Chow | 604/525 |
| 6,186,986 B1 | 2/2001 | Berg et al. | 604/264 |
| 6,193,705 B1 | 2/2001 | Mortier et al. | 604/523 |
| 6,197,015 B1 | 3/2001 | Wilson | 604/524 |
| 6,217,565 B1 | 4/2001 | Cohen | 604/525 |
| 6,254,592 B1 | 7/2001 | Samson et al. | 606/1 |
| 6,296,631 B2 | 10/2001 | Chow | 604/525 |
| 6,328,731 B1 | 12/2001 | Ouchi | 606/1 |
| 6,355,027 B1 | 3/2002 | Le et al. | 604/525 |
| 6,368,316 B1 | 4/2002 | Jansen et al. | 604/526 |
| 6,398,791 B1 | 6/2002 | Que et al. | 606/127 |
| 6,451,005 B1 | 9/2002 | Saitou et al. | 604/526 |
| 6,503,353 B1 | 1/2003 | Peterson et al. | 156/86 |
| 6,508,804 B2 | 1/2003 | Sarge et al. | 604/524 |
| 6,508,805 B1 | 1/2003 | Garabedian et al. | 604/524 |
| 6,524,303 B1 | 2/2003 | Garibaldi | 604/525 |
| 6,533,751 B2 | 3/2003 | Cragg et al. | 604/93.01 |
| 6,533,770 B1 | 3/2003 | Lepulu et al. | 604/524 |
| 6,652,508 B2 | 11/2003 | Griffin et al. | 604/526 |
| 6,706,025 B2 | 3/2004 | Engelson et al. | 604/265 |
| 2001/0034514 A1 | 10/2001 | Parker | 604/525 |
| 2002/0022831 A1 | 2/2002 | O'Connor et al. | 606/15 |

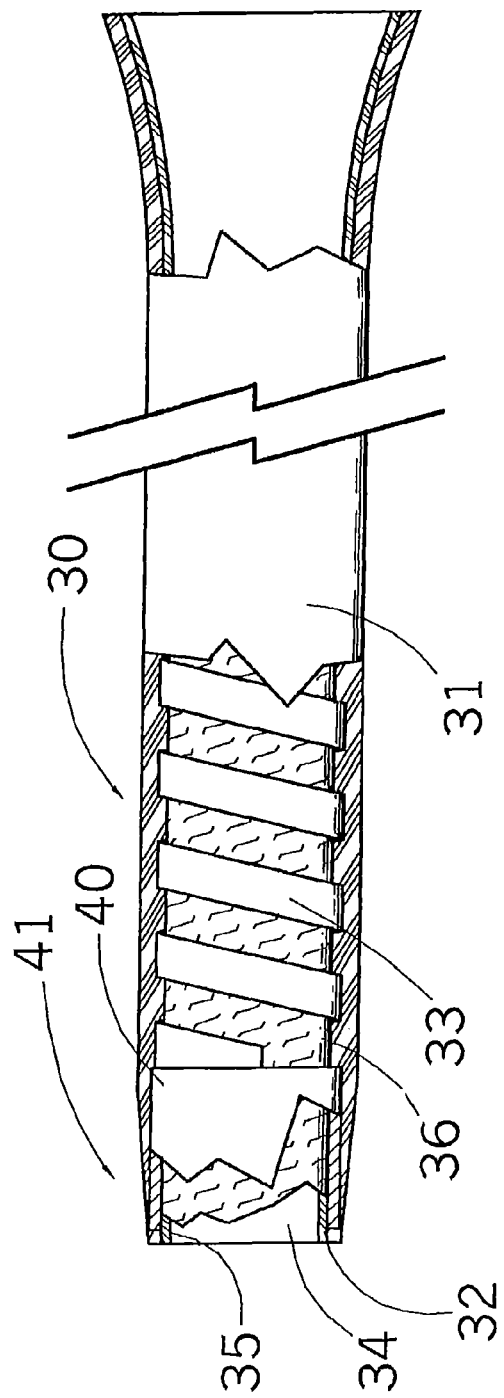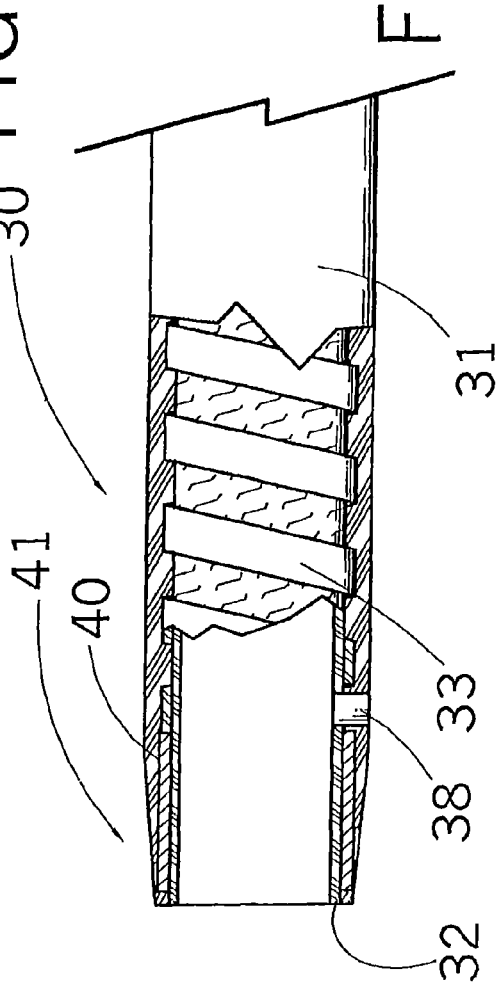

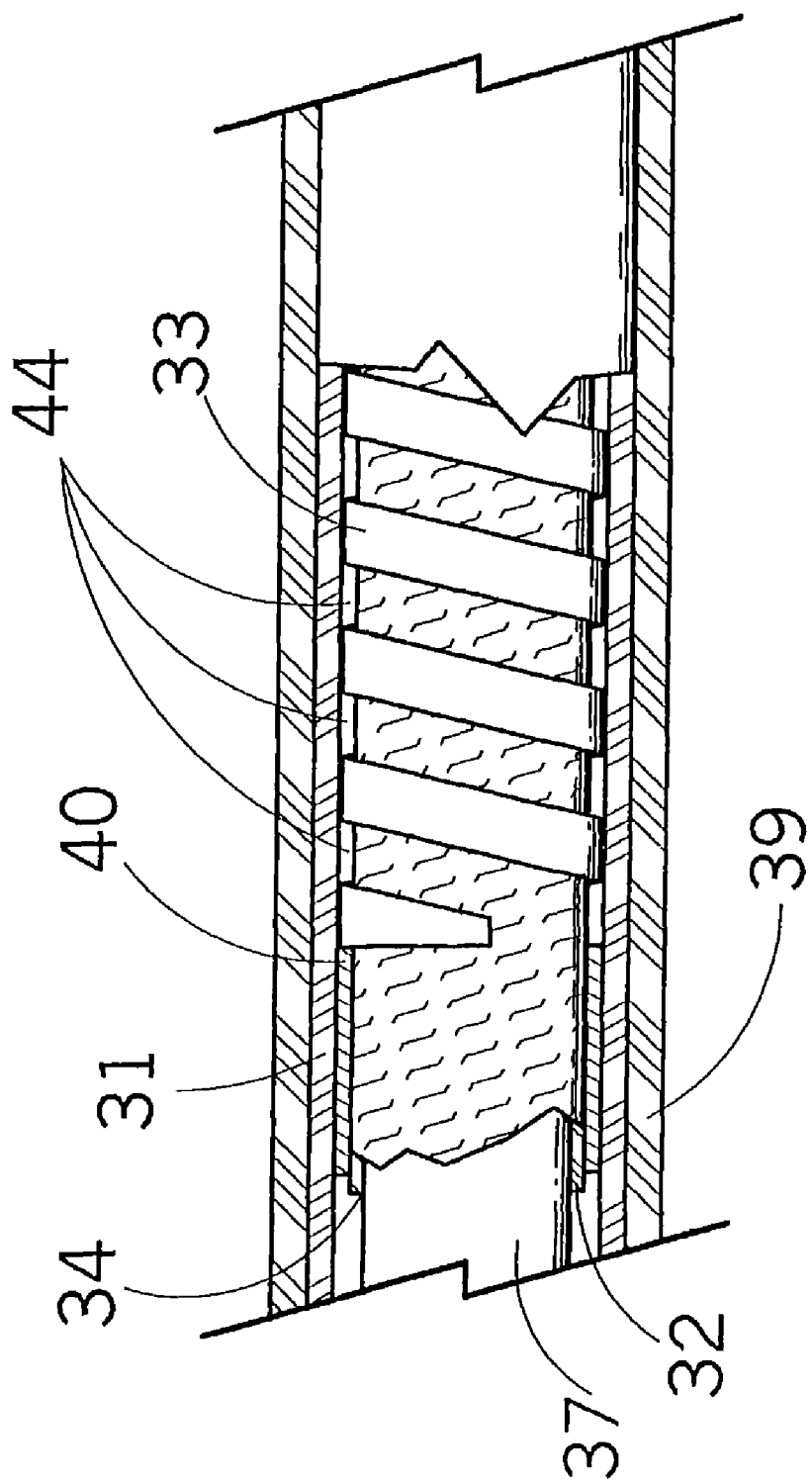

LARGE DIAMETER DELIVERY CATHETER/SHEATH

RELATED APPLICATION

This application is a divisional of application Ser. No. 10/823,176, filed Apr. 13, 2004 now U.S. Pat. No. 7,704,245, which claims the benefit of the filing date under 35 U.S.C. §119(e) of U.S. Provisional Patent Application No. 60/462,632, filed Apr. 14, 2003, both of which are hereby incorporated by reference.

BACKGROUND

1. Technical Field

This invention relates generally to delivery catheters or sheaths for providing vascular access, and more particularly, to large diameter flexible, kink-resistant introducer catheters or sheaths.

2. Background Information

Introducer sheaths are widely used as conduits to provide percutaneous access to the vascular system. Such sheaths, generally of thin-wall, small diameter construction, have a tendency to kink when traversing within the narrow confines of the vascular system. Increasing the thickness of the sheath wall minimally improves the level of kink resistance, however this level is still considered unacceptable. In addition, increasing the thickness of the sheath wall is undesirable, since it necessitates the use of a larger entry hole.

Sheaths used in certain medical procedures, such as hemofiltration and dialysis, are particularly prone to kinking, since such sheaths remain positioned in a patient's body for an extended period of time. While positioned in a patient, the sheath may be bent or pinched off and, as a result, kink due to repeated use or patient movement. A kinked sheath is unusable and cannot be straightened while positioned in the body of a patient. Consequently, the sheath must be removed, leaving an enlarged, bleeding opening which typically cannot be reused. Vascular access must then be attempted at an alternative site, and the procedure is restarted. Restarting the procedure causes a time delay, which is inconvenient, and at times may be life threatening. In addition, in some cases, an acceptable alternative site may not be available for introducing another sheath.

In addition to their use in introducing and/or withdrawing fluids from the vascular system, introducer sheaths are also utilized for delivering implantable medical devices to a deployment site well within the vascular system of a patient. Although such use of delivery catheters or sheaths is known, particular problems have been encountered when utilizing large diameter catheters or sheaths to implant medical devices. For example, large diameter catheters or sheaths are susceptible to kinking, particularly when the implantable medical device or pusher does not have a uniform diameter to reinforce the delivery catheter or sheath along its entire length. The possibility of kinking is increased when the physician exerts pressure to push the delivery catheter or sheath through an area of thrombus or calcification in the vascular system.

It is desired to provide a large diameter catheter or sheath that is less prone to kinking than existing catheters or sheaths. It is further desired to provide such a device that may be readily tracked as it is manipulated through the vascular system.

SUMMARY

The foregoing problems are solved and a technical advance is achieved in an illustrative, large diameter, flexible, kink-resistant delivery catheter or sheath. The sheath comprises an inner tube having a passageway extending longitudinally therethrough and having a diameter of from 14 to 36 French, a coil having a plurality of coil turns extending longitudinally around the inner tube, and an outer tube positioned longitudinally around the coil and the inner tube connected to inner tube through the spacings between the turns. Preferably, the sheath also includes a polymeric radiopaque marker tube disposed adjacent the coil and between the inner and outer tubes, and bonded to the outer tube.

In another form thereof, the present invention comprises a method of manufacturing an introducer sheath. The method comprises the steps of positioning an inner tube having a substantially uniform diameter of from about 14 to 36 French over a mandril; positioning a coil having a plurality of coil turns over the inner tube; positioning a polymeric radiopaque marker tube over the inner tube adjacent the distal end of the coil; and positioning a polymeric outer tube over the inner tube, coil and marker tube. A heat shrink tube then is provided to envelope the entire assembly. The heat shrink tube is heated so that a portion of the outer tube melts and flows between the coil turns to bond with said inner tube, and so that the marker tube bonds to the outer tube.

BRIEF DESCRIPTION OF THE DRAWINGS

FIG. 2 depicts a partially sectioned view of an introducer sheath of the present invention;

FIG. 3 depicts a partially sectioned view of another embodiment of the distal end of an introducer sheath of the present invention, illustrating the presence of a side port; and FIG. 4 depicts a partially sectioned view of the introducer sheath of FIG. 2, shown in combination with a heat shrink tube prior to heating.

DETAILED DESCRIPTION OF THE DRAWINGS AND THE PRESENTLY PREFERRED EMBODIMENTS

Figure 1:
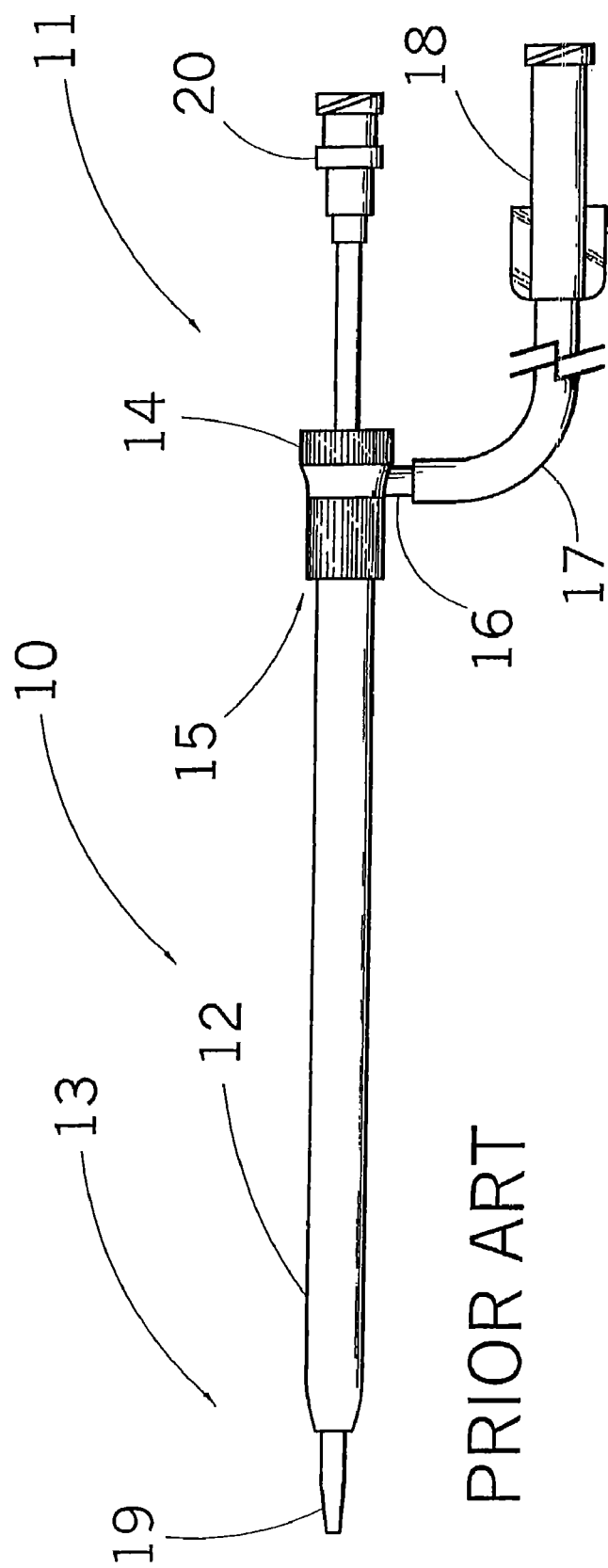
FIG. 1 depicts a prior art flexible, kink-resistant, introducer sheath shown in combination with a dilator and a connector valve.

FIG. 1 depicts an illustrative flexible, kink-resistant, introducer sheath 10. Sheath 10 includes an outer tube 12, which is provided with a tapered distal end 13, and a flared proximal end 15. In FIG. 1 sheath 10 is shown with a tapered dilator 11 that extends longitudinally through the inner passageway of the sheath, and a connector valve 14 that is attached about the proximal end of the sheath. Dilator 11 includes a tapered distal end 19 for accessing and dilating a vascular access site over a wire guide. Connector valve 14 includes a silicone disk (not shown) for preventing the backflow of fluids therethrough. The disk includes a slit for passage of the dilator therethrough in well-known fashion. Connector valve 14 includes a side arm 16 to which tube 17 and male Luer lock connector 18 may be connected for introducing and aspirating fluids through the sheath. A conventional male Luer lock connector hub 20 is attached at the proximal end of the dilator for connection to syringes and other medical apparatus. Sheaths of this general configuration are known and have been disclosed, e.g., in U.S. Pat. No. 5,380,304, incorporated by reference herein.

Depicted in FIG. 2 is a partially sectioned view of an introducer sheath 30 according to an embodiment of the present invention. This sheath may be used in combination with a dilator and connector valve as shown in FIG. 1, however, for purposes of clarity these elements have been removed from this figure. Sheath 30 comprises an inner tube 32, and a coil 33 that is wound or compression fitted around inner tube 32. An outer tube 31 is mechanically connected to a roughened outer surface 36 of the inner tube through the spacings of the coil.

Inner tube 32 is preferably formed of a lubricious material, such as a fluorocarbon. Polytetrafluoroethylene (PTFE) is an especially preferred fluorocarbon, and is well known as an inner tube or liner material in catheters and sheaths. A PTFE inner tube has a slippery inner surface 35 that allows a dilator or other medical device to be easily inserted and/or withdrawn through the inner tube. In addition, PTFE inner surface 35 is smooth and nonporous, which minimizes the formation of blood clots and other thrombi thereon. Outer surface 36 of inner tube 32 is chemically etched in well-known manner to provide the roughened surface. Roughening the outer surface enhances the connection between the inner surface of outer tube 31 and the outer surface of inner tube 32.

Preferably, inner tube 32 has a uniform inner diameter that extends the entire length of passageway 34. In this manner, the largest possible diameter catheter, stent or other interventional device can be passed through the sheath. When dealing with intravascular devices it is normally desirable to utilize a sheath having the largest possible inner diameter, and the smallest possible outer diameter, that is sufficient to achieve the intended purpose. Thus, it is desired to limit the thickness of the PTFE tube to the extent possible while, at the same time, maintaining structural integrity of the sheath and preventing the turns of compression-fitted coil 33 from protruding into inner tube passageway 34. In this regard, an inner tube having a thickness of between about 0.001 and 0.01 inch (0.025 and 0.25 mm) is preferred, more preferably between 0.003 and 0.007 inch (0.08 and 0.18 mm), and most preferably about 0.005 inch (0.13 mm).

Coil 33 may be compression fitted or wound over inner tube 32. Preferably, coil 33 is a stainless steel flat wire coil. Those skilled in the art will recognize that coils of compositions other than stainless steel that are commonly used in medical devices may be substituted. For example, coil 33 may be formed from other known metals, from a super-elastic alloy such as nitinol, or from a composite construction. In addition, coils having cross-sectional dimensions other than flat wire, such as round wire, can also be substituted. However, since it is generally desired to maintain as small a cross-sectional dimension as possible, a flat wire coil is normally preferred over a round wire coil.

In the preferred embodiment shown in FIG. 2, the flat wire coil includes uniform spacings of equal width between the turns of the coil, and the turns have a constant pitch. Generally, it is preferred that adjacent coil turns are spaced from each other by about 0.004 to 0.08 inch (0.1 to 2 mm), and more preferably, by about 0.012 inch (0.3 mm). In most cases, smaller diameter sheaths will have turns closer together, while larger diameter sheaths will have turns spaced apart a greater distance. Increasing the space between the coil turns generally increases the flexibility of a sheath, while decreasing the space between coil turns decreases the flexibility of the sheath. As well known by those skilled in the art, care must be taken to avoid spacing the turns apart by too great a distance. Such spacing would lessen the amount of support provided for the sheath, and increase the possibility of kinking.

To further advantageously control the flexibility and kink-resistance of the delivery catheter and sheath, the width and thickness of the flat wire coil can be varied. Preferably, each turn of the flat wire coil has a width (measured in the longitudinal direction of the sheath) ranging between about 0.005 and 0.030 inch (0.13 and 0.76 mm), and more preferably between about 0.012 and 0.017 inch (0.30 and 0.43 mm). In addition, the flat wire coil preferably has a thickness ranging between 0.002 and 0.010 inch (0.05 and 0.25 mm), and more preferably between about 0.004 and 0.005 inch (0.10 and 0.13 mm). Generally, wider and/or thinner coils result in greater flexibility while narrower and thicker coils result in lesser flexibility.

Although the turns of the coil shown in the preferred embodiment of FIG. 2 have uniform spacing and a constant pitch, this need not always be the case. If desired for a particular application, the coil may be provided with non-uniform spacings of the coil turns and/or the pitch of the coil turns may be varied at discrete portions of the coil. Such variance may be desired, for example, when it is desired to provide a particular segment of the coil with a flexibility that differs from the flexibility of another segment of the coil.

Preferably, the coil is spaced from the distal and proximal ends of the inner tube, to permit tapering and flaring of the respective distal and proximal ends of the sheath. In a conventional configuration in which a valve is attached at the proximal end of the sheath and a tapered tip formed at the distal end, it is preferred to terminate the coil between about 0.5 and 5.0 inches (1.27 and 12.7 cm), more preferably about 1.2 inches (3.1 cm), from the proximal end of the sheath and between about 0.1 and 2.0 inches (0.25 and 5.1 cm), more preferably about 0.8 inch (2 cm), from the distal end.

Outer tube 31 can be formed of any well-known polymer commonly used for such purpose. Preferably, outer tube 31 comprises a heat shrinkable polyamide material, such as nylon. An outer tube having a pre-shrink thickness between about 0.004 and 0.014 inch (0.10 and 0.36 mm) is preferred. For large diameter sheaths of relatively smaller French size, such as 14 French and 16 French, a pre-shrink thickness between about 0.004 and 0.008 inch (0.10 and 0.20 mm) is preferred. For large diameter sheaths having a French size of 18-24 French, a pre-shrink thickness between about 0.006 and 0.014 inch (0.15 and 0.36 mm) is preferred, and more particularly between about 0.008 and 0.012 inch (0.20 and 0.30 mm). Sheaths larger than 24 French would normally have correspondingly larger thicknesses. The heat shrink process normally causes a slight reduction is thickness, thus, the post-shrink thickness in most cases will be slightly less than the pre-shrink thickness.

It is important that the material of outer tube 31 be sufficiently flexible so that the sheath can navigate the tortuous pathways encountered in the vascular system. Prior art small diameter sheaths, referred to herein as sheaths having a diameter of about 5 to 12 French, generally include an outer layer or jacket primarily comprised of a material having a high durometer, such as a durometer between about 60 and 80 on the Shore D scale. Such high durometer materials provide favorable kink resistance to the sheath, and also provide sufficient strength to enable the small diameter sheath to be guided through small diameter passageways in the vasculature. Using this same high durometer material with a large diameter sheath, referred to herein as a sheath having a diameter of about 14 to 36 French, or larger, would still result in a sheath that is kink resistant, but one that is more difficult to bend in actual practice than are smaller size sheaths. In some applications, this lack of flexibility may preclude use of the large diameter sheath altogether, or at a minimum, add a degree of difficulty and uncertainty to the procedure that would not be present if a more flexible sheath was used. Thus, such large diameter sized sheaths as described herein advantageously include a softer (e.g., lower durometer) outer jacket material when compared to the jacket material commonly used in small diameter sheaths. This softer outer jacket allows large diameter sheaths to bend more easily when inserted into the vasculature.

Outer tube 31 is preferably formed of a nylon elastomer having a durometer of about 30 to 60 on the Shore D hardness scale, more preferably about 35 to 50, and most preferably about 40. Although nylon tubing having a durometer as low as about 20 may be used in inventive large diameter sheaths as described herein, sheaths formed from such low durometer tubing can be difficult to manufacture. Outer layer materials having a high durometer up to about 85 may be acceptable in inventive large diameter (14 to 36 French) sheaths in some applications, such as when there is little tortuousity in the vessels to be traversed or when there is little or no need for enhanced flexibility. However, in actual practice, this will rarely be the case, and the flexibility of such high durometer large diameter sheaths will be inferior when compared to sheaths having a durometer of about 40. In some applications the lack of flexibility of the high durometer sheath would preclude its use altogether. While outer tubes of numerous durometers may be acceptable and are considered within the scope of the invention, it is believed that an outer layer having a durometer of about 40 provides best results because it combines the advantages of ease of manufacturing with sufficient flexibility in a wide variety of applications.

Those skilled in the art will recognize that there is a trade-off between flexibility and ease of manufacturing. If a sheath is to be used for a purpose that does not require that the sheath be highly flexible, then a higher durometer sheath may be used. On the other hand, if flexibility is a primary concern, then a sheath with an outer tube 31 having a durometer of 40, or even lower, should be used.

A radiopaque marker 40 may be positioned over the distal end of the inner tube next to flat wire coil 33. Radiopaque marker 40 comprises an elastomer, such as nylon. Preferably, marker 40 has a formulation similar to or the same as that of outer tube 31 to enhance thermal bonding during the heat shrink process. Also, it is preferred that the durometer of the elastomer is similar to or the same as that of the outer tube. In this manner, the flexibility of the sheath is not adversely affected by the presence of the marker. The percent filler of radiopaque material in the marker may vary depending on the loading capacity of the particular elastomer used. For a nylon marker having a durometer of about 40, the radiopaque loading may be between about 40 and 90 wt %, preferably about 80 wt %, of the total weight of the radiopaque marker.

Preferably, the radiopaque material is a material commonly used for such purposes, such as tungsten. However the radiopaque material may comprise any well-known radiopaque filler material that is compatible with the matrix of the radiopaque marker, and that may be loaded in the matrix at sufficiently high loading levels to enable an operator to distinguish the marker from the remainder of the sheath under fluoroscopy. Those of ordinary skill in the art are familiar with acceptable techniques for loading radiopaque particles in a polymeric material.

If desired, a side port 38 can be provided as shown in FIG. 3. Side port 38 can be used to inject or infuse contrast media into the vascular system for radiographic visualization of the delivery catheter or sheath and contained medical device. Side port 38 may also be used to prepare an implantable device with a saline or a similar solution, to reduce the chances of embolism/clotting. In this embodiment, side port 38 is provided at the distal end of the reinforcement or flat wire coil and through the inner and outer tube as well as the radiopaque marker tube, although those skilled in the art will recognize that the positioning of side port 38 may be varied according to its intended purpose.

During assembly of sheath 30, inner tube 32 is fitted over a suitably-sized mandril 37 as illustrated in FIG. 4. Coil 33 is compression fitted or wound around inner tube 32. Suitable techniques for compression fitting and winding a coil around a tube are well known in the art. Radiopaque marker tube 40 is then positioned over the inner tube adjacent the distal end of the compression fitted coil. Outer tube 31 is disposed or positioned over the coil and the inner and marker tubes, and the entire assembly is then enveloped in a heat shrink tube 39. At this time, a space 44 exists between outer tube 31 and inner tube 32, as well as between the turns of the coil. The entire assembly is then baked in an oven, whereupon outer tube 31 begins to melt. A melted portion of tube 31 flows between the coil turns in well known fashion, and is mechanically connected to the roughened outer surface 36 of inner tube 32. Heat-formable outer nylon tube 31 is essentially self-leveling after heating, which provides a uniform outer diameter to the outer tube. Once outer tube 31 is heat shrunk onto the roughened surface of inner tube 32, the heat shrink tube is split and cut off, and the mandril is removed. During the heat shrink process, the outer surface of elastomeric radiopaque marker 40 bonds with the inner surface of outer layer 31, while the inner surface of marker 40 bonds with the roughened outer surface of inner tube 32.

After the heat shrink tube has been removed, the distal end of the large diameter delivery catheter or sheath can be cut off approximately 0.1 to 2 inches (0.25 and 5.1 cm) beyond the distal end of the coil. The outer and marker tubes can be beveled or ground, or heat-molded, to provide a tapered distal end 41 that enables the delivery catheter tube to more easily traverse the vasculature of a patient. The proximal end of the delivery catheter or sheath extends approximately 0.5 to 5.0 inches (1.27 and 12.7 cm) past the proximal end of the coil, which can be cut and flared in known manner for positioning a hub or valve thereon to provide a leak resistant or hemostatic condition during insertion into a patient. Other details of the construction of the sheath are conventional, and are discussed, e.g., in the incorporated-by-reference U.S. Pat. No. 5,380,304.

By way of example, a large diameter delivery catheter having a 22 French passageway can have a length of about 54 inches (137 cm). The inner diameter of a 22 French sheath is about 0.288 in (7.3 mm). Inner tube 32 comprises PTFE and has a wall thickness of about 0.005 inch (0.13 mm). Stainless steel flat wire coil 33 may be wound or compression fitted around outer surface 36 of inner tube 32 approximately 0.12 to 0.16 inch (3 to 4 mm) from the distal end thereof and approximately 0.2 inch (5 mm) from the proximal end thereof to taper and flare the distal and proximal ends, respectively. The coils have a thickness of about 0.005 inch (0.13 mm) and a width of about 0.017 inch 0.43 mm). Outer tube 31 comprises nylon that is heat shrunk over coil 33. Outer tube 31 has an outer diameter of about 0.335 inch (8.5 mm) and a durometer of about 40. The thickness of the nylon tube is approximately 0.01 inch (0.25 mm). The thickness of the radiopaque marker is about 0.005 inch (0.13 mm).

Respective 18, 20 and 24 French sheaths may be formed from the same components used to form the 22 French sheath. The PTFE inner layer can have the same wall thickness, and the coil can have the same specifications as the coil used in the 22 French sheath. With a 14 and a 16 French sheath, it is preferred to have a thinner PTFE layer. A 24 French sheath has an inner diameter of about 0.315 in (8.0 mm).

Such large diameter delivery catheters or sheaths as described herein provide for the delivery of large diameter devices to, for example, the aorta and iliac arteries. Examples of such implantable medical devices include stents and stent-graft devices for the repair or exclusion of aneurysms. Such sheaths preferably have a diameter of from about 14 to 36 French, even more preferably from 14 to 26 French and most preferably 22 or 24 French.

It is contemplated that various other materials may be utilized for the inner, outer, and heat shrink tubes. It is also contemplated that introducer sheaths with an inside diameter ranging in size from 14 to 36 French, or even larger, are readily producible and may be considered within the scope of the invention. In summary, the flexible, kink-resistant, introducer sheath provides a large diameter thin-wall sheath that is extremely kink-resistant for long-term use applications.

It is therefore intended that the foregoing detailed description be regarded as illustrative rather than limiting, and that it be understood that it is the following claims, including all equivalents, that are intended to define the spirit and scope of this invention.

What is claimed is:

1. A method of manufacturing an introducer sheath, comprising the steps of:
    positioning a lubricious inner tube over a mandril, said inner tube having a substantially uniform inner diameter of from about 16 to 30 French, said inner tube having a wall thickness between about 0.001 and 0.01 inch (0.025 and 0.25 mm);
    positioning a coil over said inner tube, said coil having a plurality of turns extending longitudinally around a length of said inner tube, and a plurality of spacings between said turns, said spacings having a generally uniform width along said inner tube length;
    positioning a polymeric outer tube over said inner tube and coil, said outer tube having a durometer of about 30 to 60 on the Shore D hardness scale, and having a wall thickness between about 0.004 and 0.014 inch (0.10 and 0.36 mm);
    positioning a heat shrink tube over a sheath assembly comprising the inner tube, coil, and outer tube;
    heating said heat shrink tube and sheath assembly so that a portion of said outer tube melts and flows between said coil turns to bond with an outer surface of the inner tube; and
    removing said mandril and said heat shrink tube.

2. The method of claim 1, further comprising the step of positioning a polymeric radiopaque marker tube over said inner tube adjacent a distal end of said coil, wherein said polymeric outer tube is positioned over said inner tube, coil, and marker tube, and wherein said polymeric outer tube is bonded to said marker tube upon said heating of said sheath assembly.

3. The method of claim 2, wherein said marker tube comprises a high density radiopaque material ranging between about 40 and 90 weight percent of the total weight of the marker tube.

4. The method of claim 2, wherein each of said outer tube and radiographic marker tube is formed of polyamide, and each of said tubes has a durometer between about 35 and 50 on the Shore D scale.

5. The method of claim 2, wherein said radiographic marker tube and said outer tube are formed from the same polymer.

6. The method of claim 1, wherein said coil comprises flat wire, and wherein said uniform width of said coil spacings is between about 0.004 and 0.08 inch (0.1 and 2 mm).

7. The method of claim 6, wherein a proximal end of said coil is spaced from a proximal end of said sheath by about 0.5 to 5.0 inches (1.27 and 12.7 cm), and a distal end of said coil is spaced from a distal end of said sheath by about 0.1 to 2 inches (0.25 and 5.1 cm).

8. The method of claim 1, wherein said substantially uniform inner diameter ranges from 18 to 24 French.

9. The method of claim 1, wherein said substantially uniform inner diameter ranges from 20 to 26 French.

10. The method of claim 9, wherein said diameter comprises one of 22 French and 24 French.

11. The method of claim 9, wherein said inner tube comprises PTFE, said coil comprises stainless steel flat wire, said outer tube comprises a polyamide, and said outer tube has a durometer of about 35 to 50 on the Shore D hardness scale.

12. A method of manufacturing an introducer sheath, comprising the steps of:
    positioning an inner tube over a mandril, said inner tube having a substantially uniform inner diameter of from about 18 to 24 French, said inner tube having a wall thickness between about 0.001 and 0.01 inch (0.025 and 0.25 mm);
    positioning a flat wire coil over said inner tube, said flat wire coil having a plurality of turns having substantially uniform spacings therebetween, wherein said width of said coil spacings is about 0.012 inch (0.3 mm), a proximal end of said coil being spaced from a proximal end of said sheath by about 1.2 inches (3.1), and a distal end of said coil is spaced from a distal end of said sheath by about 0.8 inch (2 cm);
    positioning a polymeric radiopaque marker tube over said inner tube adjacent a distal end of said flat wire coil, said marker tube comprising a high density radiopaque material ranging between about 40 and 90 weight percent of a total weight of the marker tube;
    positioning a polymeric outer tube over said inner tube, coil, and marker tube, said outer tube having a durometer between about 35 and 50 on the Shore D hardness scale, and having a wall thickness between about 0.004 and 0.014 inch (0.10 and 0.36 mm);
    positioning a heat shrink tube over the outer tube, coil, marker tube, and inner tube;
    heating said heat shrink tube so that a portion of said outer tube melts and flows between said coil turns to bond with said inner tube, and so that said marker tube bonds to said outer tube; and
    removing said mandril and said heat shrink tube.

* * * * *